United States Patent
Le Cain et al.

(10) Patent No.: US 12,282,207 B2
(45) Date of Patent: Apr. 22, 2025

(54) METHOD FOR DETERMINING A COMPONENT OF AN OPHTHALMIC EQUIPMENT AND ASSOCIATED SYSTEM

(71) Applicant: Essilor International, Charenton-le-Pont (FR)

(72) Inventors: Aurélie Le Cain, Charenton-le-Pont (FR); Sébastien Fricker, Charenton-le-Pont (FR); Konogan Baranton, Charenton-le-Pont (FR)

(73) Assignee: Essilor International, Charenton-le-Pont (FR)

( * ) Notice: Subject to any disclaimer, the term of this patent is extended or adjusted under 35 U.S.C. 154(b) by 710 days.

(21) Appl. No.: 17/255,727

(22) PCT Filed: Jul. 18, 2019

(86) PCT No.: PCT/EP2019/069436
§ 371 (c)(1),
(2) Date: Dec. 23, 2020

(87) PCT Pub. No.: WO2020/016381
PCT Pub. Date: Jan. 23, 2020

(65) Prior Publication Data
US 2021/0271107 A1    Sep. 2, 2021

(30) Foreign Application Priority Data

Jul. 18, 2018  (EP) .................................. 18305981

(51) Int. Cl.
*G02C 7/02*   (2006.01)
*G06N 20/00*  (2019.01)
*G16H 10/20*  (2018.01)

(52) U.S. Cl.
CPC ............. *G02C 7/027* (2013.01); *G06N 20/00* (2019.01); *G16H 10/20* (2018.01)

(58) Field of Classification Search
CPC ......... G02C 7/027; G16H 10/20; G06N 20/00
(Continued)

(56) References Cited

U.S. PATENT DOCUMENTS

2003/0107707 A1   6/2003  Fisher et al.
2014/0347265 A1   11/2014 Aimone et al.
(Continued)

OTHER PUBLICATIONS

International Search Report and Written Opinion issued on Sep. 30, 2019 in PCT/EP2019/069436 filed on Jul. 18, 2019.

*Primary Examiner* — Sharrief I Broome
(74) *Attorney, Agent, or Firm* — Oblon, McClelland, Maier & Neustadt, L.L.P.

(57) ABSTRACT

A method for determining a component of an ophthalmic equipment, the method including acquiring a set of parameter values relating to the given wearer, processing the acquired set of parameter values to infer a group, the given wearer belonging to the inferred group and the inferred group belongs to a plurality of pre-established groups, the pre-established groups being elaborated based on respective sets of parameter values of a plurality of reference wearers. The method further including determining, based on the inferred group, at least a feature enabling to determine a component of an ophthalmic equipment of the given wearer, and determining a component of an ophthalmic equipment to be used by the wearer based on the at least a determined feature, each set of parameters values of the plurality of reference wearers including parameter values belonging to at least two distinct categories.

13 Claims, 1 Drawing Sheet

(58) Field of Classification Search
USPC .......................... 351/159.01, 159.02, 159.51
See application file for complete search history.

(56) References Cited

U.S. PATENT DOCUMENTS

| | | | |
|---|---|---|---|
| 2015/0055085 A1* | 2/2015 | Fonte | B29D 12/02 |
| | | | 700/98 |
| 2015/0055086 A1 | 2/2015 | Fonte et al. | |
| 2015/0154322 A1 | 6/2015 | Fonte et al. | |
| 2015/0154678 A1* | 6/2015 | Fonte | G16B 5/00 |
| | | | 705/26.5 |
| 2015/0154679 A1 | 6/2015 | Fonte et al. | |
| 2015/0212343 A1 | 7/2015 | Fonte et al. | |
| 2016/0062151 A1 | 3/2016 | Fonte et al. | |
| 2016/0062152 A1 | 3/2016 | Fonte et al. | |
| 2016/0299360 A1* | 10/2016 | Fonte | G02C 7/027 |
| 2017/0068121 A1 | 3/2017 | Fonte et al. | |
| 2017/0269385 A1 | 9/2017 | Fonte et al. | |
| 2017/0299888 A1* | 10/2017 | Tranvouez | G02C 7/024 |
| 2017/0371178 A1* | 12/2017 | Crespo | G02C 7/024 |
| 2018/0103903 A1 | 4/2018 | Tzvieli et al. | |
| 2018/0116502 A1* | 5/2018 | Ishinabe | A61B 3/117 |
| 2018/0299704 A1 | 10/2018 | Fonte et al. | |
| 2019/0146246 A1 | 5/2019 | Fonte et al. | |

* cited by examiner

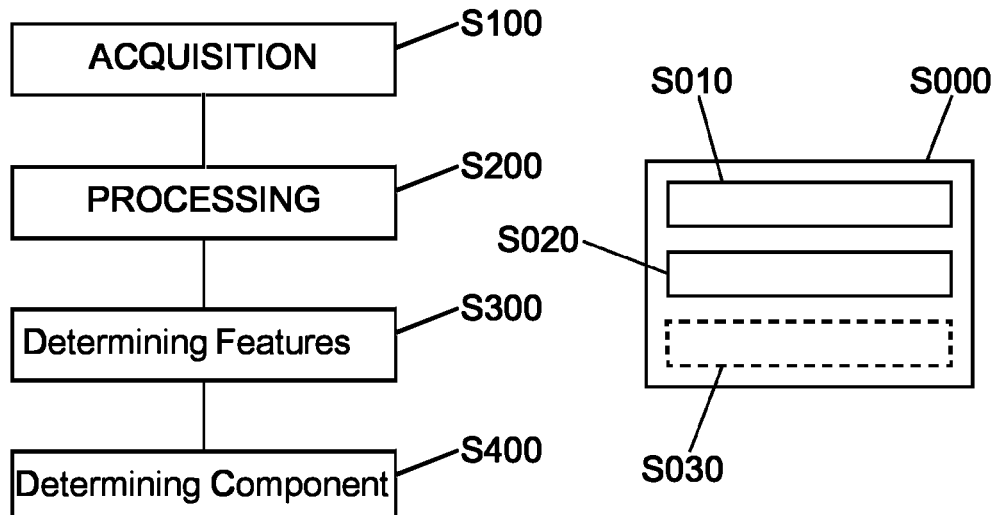
FIG. 1A
FIG. 1B
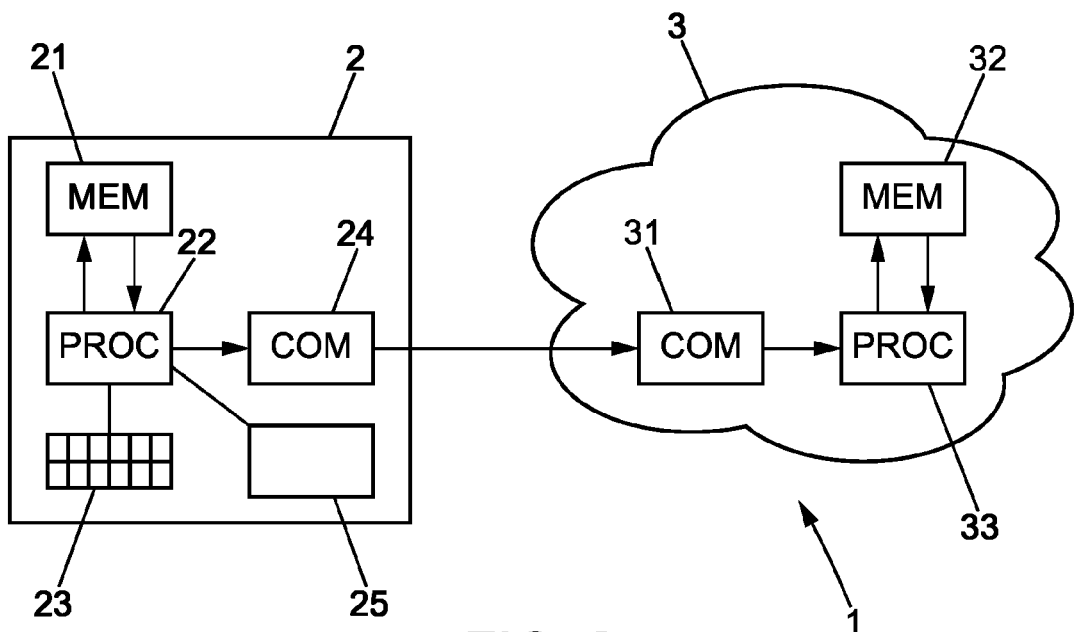
FIG. 2

METHOD FOR DETERMINING A COMPONENT OF AN OPHTHALMIC EQUIPMENT AND ASSOCIATED SYSTEM

FIELD OF THE INVENTION

The present invention relates to the determination of an ophthalmic equipment that is adapted to a given wearer and in particular, of at least a component of an ophthalmic equipment.

BACKGROUND OF THE INVENTION

The ophthalmic equipment is usually a pair of glasses and comprises a plurality of components. One of the components is the ophthalmic lens. Determining an ophthalmic lens that is adapted to a given wearer and which provides a good satisfaction of the wearer is quite difficult. A reason for the difficulties encountered is the multiplicity of parameters related to the wearer to take into account. Another problem is the multiplicity of parameters to determine in order to determine an ophthalmic lens that is particularly adapted to the given wearer.

In order to simplify the determination of a component, a segmentation may be used. The segmentation consists in determining at least a feature of the component based on a parameter that is easily accessible to the wearer.

At the moment, an ophthalmic lens may be determined based on only one parameter relating to the wearer such as the ethnicity which enable to determine the wearing conditions, the handedness which enables to determine the vision zones positioning, the gender which enable to determine the wearing conditions, the size which enables to determine the reading distance. Currently, the segmentation is only based on one input variable and is quite limited. It is in fact difficult to determine a component of an ophthalmic equipment based on a plurality of parameters relating to the wearer when those parameters may not be used directly to determine the component of the ophthalmic equipment.

PRESENTATION OF THE INVENTION

In view of the above, one aim of the invention is to alleviate at least part of the inconveniences of the prior art.

In particular, one aim of the invention is to allow the determination of a component of an ophthalmic equipment based on a plurality of parameters that are easily accessible to the wearer or the eyecare professional but may not be used directly to determine the component.

To this end, it is proposed, according to a first aspect, a method for determining a component of an ophthalmic equipment among a set of components of an ophthalmic equipment for a given wearer, the method comprising:
  acquiring a set of parameter values relating to the given wearer,
  processing said acquired set of parameter values to infer a group, wherein the given wearer belongs to the inferred group and the inferred group belongs to a plurality of pre-established groups, the pre-established groups being elaborated based on respective sets of parameter values of a plurality of reference wearers,
  determining, based on the inferred group, at least a feature enabling to determine a component of an ophthalmic equipment of the given wearer, wherein the component belongs to the set of components of an ophthalmic equipment, and
  determining a component of an ophthalmic equipment to be used by the wearer based on at least a determined feature,
  wherein each set of parameters values of the plurality of reference wearers comprises parameter values belonging to at least two distinct categories.

It may be noted that a plurality of components of the ophthalmic equipment may be determined according to the method of the invention.

According to an embodiment, the categories are relative to at least one of: an ethnicity of the wearer, a gender of the wearer, an age of the wearer, a biometric parameter of the wearer, an activity of the wearer, an environment of the wearer, a clothing style of the wearer, a postural behavior of the wearer, features of at least one component of an ophthalmic equipment previously or currently worn by the wearer, prescription data of the wearer.

According to an embodiment, each set of parameter values of the plurality of reference wearers further comprises the value of at least one feature enabling to determine a component of an ophthalmic equipment of each reference wearer.

According to an embodiment, each set of parameters values of the plurality of reference wearers further comprises at least an additional parameter value and at least an additional parameter value of the given wearer is determined based on the values of said additional parameter of the reference wearers belonging to the inferred group.

According to an embodiment, the sets of parameter values of the plurality of reference wearers comprise new sets of parameter values of new reference wearers, and the pre-established groups are periodically actualized based on the sets of parameter values of the plurality of reference wearers comprising new sets of parameter values.

According to an embodiment, the acquired set of parameter values of the given wearer comprises a set of input parameter values of the given wearer and determining at least a feature comprises running a prediction model on the set of input parameter values of the given wearer.

According to an embodiment, the prediction model is elaborated by machine learning based on respective sets of input parameter values of the plurality of reference wearers and on the value of at least one feature of a component of an ophthalmic equipment of each of the plurality of reference wearers belonging to the inferred group.

According to an embodiment, the pre-established groups are elaborated by machine learning based on the respective sets of parameter values of the plurality of reference wearers.

According to an embodiment, processing said acquired set of parameter values comprises determining at least one range to which a parameter value belongs and inferring the group to which the wearer belongs based on the determined range.

According to an embodiment, the acquired parameter values are measured and/or obtained from a questionnaire or a data base, or extracted from online data of the wearer.

According to an embodiment, the components of an ophthalmic equipment are chosen from one of:
  an ophthalmic lens design, wherein a lens design comprises a set of optimization parameters and/or a set of instructions configured to be used in conjunction with the prescription data to determine at least one surface of an ophthalmic lens,
  a material of an ophthalmic lens,
  at least a post-treatment layer, the post treatment layer being one of a variably or permanently tinted layer, an anti-breakage layer, an anti-scratch layer, an anti-reflection layer, an anti-smudge layer or an anti-fog layer,
a frame shape or material,
a control mode for an active lens,
an augmented reality equipment having a particular design.

It is also proposed, according to a second aspect, a computer program product, comprising a series of instructions that is accessible to a processor and which, when executed by the processor, causes the processor to perform the steps of the method previously described.

It is also proposed, according to a third aspect, a storage medium having thereon a computer program comprising program instructions, the computer program being loadable into a processor and adapted to cause the processor to carry out, when the computer program is run by the processor, the method previously described.

It is also proposed, according to a fourth aspect, System for determining at least a component of an ophthalmic equipment among a set of components of an ophthalmic equipment, the system being configured to implement the method previously described and comprising:
  a collecting unit configured to acquire a set of parameter values relating to the given wearer, and
  a centralized treatment unit configured to:
    receive from the collecting unit the set of parameter values relating to the given wearer,
    process said acquired set of parameter values to infer a group, wherein the given wearer belongs to the inferred group, wherein the inferred group belongs to a plurality of pre-established groups, the pre-established groups being elaborated based on respective sets of parameter values of a plurality of reference wearers,
    determine, based on the inferred group, at least a feature enabling to determine a component of an ophthalmic equipment of the given wearer, wherein the component belongs to the set of components of an ophthalmic equipment, and
    determine a component of an ophthalmic equipment to be used by the wearer based on at least a determined feature,
  wherein each set of parameters values of the plurality of reference wearers comprises parameter values belonging to at least two distinct categories.

The expression "at least a feature enabling to determine a component of an ophthalmic equipment of the given wearer" should be understood in a broad sense and may be at least a feature of the component or at least a design parameter that enables to determine the component. This expression may also refer to the component itself when all the features of the component may be determined based on the inferred group.

According to the invention, it is possible, based on a limited set of parameter values relating to the wearer to determine a component that is adapted for the given wearer. Further, the features enabling to determine a component of the ophthalmic equipment of the given wearer are chosen based on the similarity of the wearer with some of the reference wearers. Thus, the best possible component may be proposed to the given wearer.

BRIEF DESCRIPTION OF THE DRAWINGS

Further details, aspects and embodiments of the proposed solution will be described, by way of example only, with reference to the drawings.

FIG. 1A illustrates the method of determining at least a component of an ophthalmic equipment according to the invention.

FIG. 1B illustrates how the pre-established groups of wearers are established.

FIG. 2 illustrates an embodiment of a system for determining at least a component of an ophthalmic equipment according to an embodiment.

DESCRIPTION

FIG. 1A illustrates the method of determining at least a component of an ophthalmic equipment according to the invention.

The method comprises an acquisition step S100, a processing step S200, a first determining step S300 and a second determining step S400.

The acquisition step S100 comprises acquiring a set of parameter values relating to a given wearer. At least part of the parameter values may be measured and/or obtained from a questionnaire or from a data base and/or extracted from online data of the wearer.

Preferably, the parameter values relating to a given wearer comprise parameter values belonging to at least two distinct categories. Preferably, the categories are relative to at least one of: an ethnicity of the wearer, a gender of the wearer, an age of the wearer, a biometric parameter of the wearer, an activity of the wearer, an environment of the wearer, a clothing style of the wearer, a postural behavior of the wearer, features of at least one component of an ophthalmic equipment previously or currently worn by the wearer, prescription data of the wearer.

The processing step S200 comprises processing said acquired set of parameter values to infer a group of wearers, wherein the given wearer belongs to the inferred group, wherein the inferred group belongs to a plurality of pre-established groups, wherein the pre-established groups are elaborated based on respective sets of parameter values of a plurality of reference wearers. The pre-established groups are elaborated in an initialization step S000 which is described in reference to FIG. 1B.

The first determining step S300 comprises determining based on the inferred group, at least a feature enabling to determine a component of an ophthalmic equipment of the given wearer, wherein the component belongs to the set of components of an ophthalmic equipment.

Preferably, the components of an ophthalmic equipment are chosen from one of:
  an ophthalmic lens design, wherein a lens design comprises a set of optimization parameters and/or a set of instructions configured to be used in conjunction with the prescription data to determine at least one surface of an ophthalmic lens,
  a material of an ophthalmic lens,
  at least a post-treatment layer, the post treatment layer being one of a variably or permanently tinted layer, an anti-breakage layer, an anti-scratch layer, an anti-reflection layer, an anti-smudge layer or an anti-fog layer,
  a frame shape or material,
  a control mode for an active lens,
  an augmented reality equipment having a particular design.

The second determining step S400 comprises determining at least a component of an ophthalmic equipment to be used by the wearer based on at least a determined feature of step S300. According to an embodiment, which is described in reference to embodiment 2, the second determining step S400 may comprise determining a plurality of components of an ophthalmic equipment It may be noted that the at least a feature enabling to determine a component of an ophthalmic equipment of the given wearer may be a feature of the component. In that case, when other features are needed to determine the component, the component is determined in step S400. In other embodiments, all the features of the component are determined in step S300 and the step S400 of determining the component is comprised within the step S300 of determining at least a feature enabling to determine a component of an ophthalmic equipment of the given wearer. In other embodiments, the at least a feature enabling to determine a component of an ophthalmic equipment of the given wearer is a design parameter that enables to determine the component. This case is illustrated in reference to embodiment 3.

FIG. 1B illustrates how the pre-established groups of wearers are established. The pre-established groups are established in an initialization step S000 which is conducted prior to the method of FIG. 1A.

The initialization step S000 comprises a sub-step S010 in which sets of parameter values of a plurality of reference wearers are collected and a sub-step S020 in which a plurality of groups of wearers having at least some similar parameter values are established based on respective sets of parameter values of the plurality of reference wearers.

Preferably, the parameter values of the plurality of reference wearers are obtained from a data base. According to the invention, each set of parameters values of the plurality of reference wearers comprises parameter values belonging to at least two distinct categories. Preferably, the categories are relative to at least one of: an ethnicity of the wearer, a gender of the wearer, an age of the wearer, a biometric parameter of the wearer, an activity of the wearer, an environment of the wearer, a clothing style of the wearer, a postural behavior of the wearer, features of at least one component of an ophthalmic equipment previously or currently worn by the wearer, prescription data of the wearer.

The plurality of groups of reference wearers may be established through clustering or classification on at least part of the parameter values of the plurality of reference wearers. Preferably, the plurality of groups of reference wearers is obtained by machine learning but other methods may be used.

Clustering, also referred to as unsupervised classification, may be performed using k-means or Ascending Hierarchical Classification (AHC). Classification, also referred to as supervised classification, may be performed by implementing decision trees, neural networks and gradient boosting, for example. Preferably, classification is performed on the basis of the value of at least one feature enabling to determine a component of an ophthalmic equipment of each reference wearer, said at least one feature being comprised within the set of parameter values of the plurality of reference wearers.

Optionally, the initialization step S000 may comprise a sub-step S030 of associating at least a feature enabling to determine a component of an ophthalmic equipment to each group of the plurality of groups of step S020. In other embodiments, the value of the at least one feature enabling to determine a component of an ophthalmic equipment of the given wearer is determined in step S300 of the method of FIG. 1A based on the respective set of parameter values of the reference wearers belonging to the inferred group.

According to an embodiment, the sub-steps S010 of collecting the sets of parameter values of the plurality of reference wearers and S020 of establishing the plurality of groups of wearers are periodically executed so that the sets of parameter values of the plurality of reference wearers comprise new sets of parameter values of new reference wearers, and the plurality of groups of wearers are periodically actualized based on the sets of parameter values of the plurality of reference wearers comprising new sets of parameter values.

FIG. 2 illustrates an embodiment of a system for determining at least a component of an ophthalmic equipment according to an embodiment.

The system 1 comprises a collecting unit 2 and a centralized treatment unit 3. The collecting unit 2 is configured to acquire a set of parameter values relating to the given wearer. The collecting unit 2 comprises a memory 21, a processor 22, a keyboard 23, a communication interface 24 and a display 25. In this embodiment, the set of parameter values of the given wearer are obtained from a questionnaire which is stored in the memory 21 and displayed by the display 25 using instructions stored in the memory 21 and executed by the processor 22. The answers of the given wearer are entered using the keyboard 23, for example, and are processed by the processor 22 in order to send them to the centralized treatment unit 3.

The centralized treatment unit 3 comprises a communication interface 31, a memory 32 and a processor 33.

The centralized treatment unit 3 is configured to:
receive from the collecting unit 2 the set of parameter values relating to the given wearer via its communication interface 31, and
execute the steps S200 to S400 of FIG. 1A to determine at least a component of an ophthalmic equipment of the given wearer.

A set of instructions corresponding to steps S200 to S400 are stored in the memory 32 and executed by the processor 33.

The centralized treatment unit 3 is also configured to execute the initialization step S000 of FIG. 1B when the set of parameter values of the plurality of reference wearers is stored in the memory 32.

It may be noted that the collecting unit 2 may be a smartphone, in which case, the keyboard is replaced by a keypad, or a personal computer belonging to the eyecare specialist, the given wearer filling in the questionnaire in the shop of the eyecare professional. The centralized treatment unit 3 is then a server connected to the collecting unit via the internet. Preferably, the server is part of a cloud network.

According to another embodiment, the collecting unit 2 may acquire the set of parameter values relating to the given wearer from a data base, or extract them from online data of the wearer.

Below are described some non-limiting embodiments of the invention for illustration purposes. It may be noted that some steps of the method of FIG. 1A and FIG. 1B may be used in other embodiments.

Embodiment 1: Determination of a Combination of Post-Treatment Layers to be Applied on the Ophthalmic Lens Based on Environmental Conditions and Type of Activity Performed by the Wearer According to an embodiment, it may be relevant to choose a combination of post-treatment layers to be applied on an ophthalmic lens depending on the type of environment to which the wearer is submitted and on the type of activity the wearer performs.

A combination of post-treatment layers may comprise a combination of:
- a variably or permanently tinted layer,
- an anti-breakage layer, also called hard coat,
- an anti-scratch layer,
- an anti-reflection layer, and
- an anti-smudge layer, also called top coat, which is oleophobic in order to avoid having finger marks on the ophthalmic lens and also hydrophobic in order to be water-repellent.

The anti-smudge layer, which is water-repellent is not compatible with an anti-fog layer which aims at providing an homogenous layer of water on the ophthalmic lens. The anti-smudge layer may thus be replaced by an anti-fog layer.

Some of those layers are optional like the tinted layer, the anti-reflection layer, for example.

The type of environment in which the wearer lives may be inferred from the geographical region or the city in which the wearer lives. The type of environment may be defined by environmental conditions which may comprise the considered temperature, hygrometry and UV doses, for example, and may be used to choose a combination of post-treatment layers which is particularly adapted to the given wearer.

The type of activity the wearer performs may also have an influence on the choice of some layers of the combination of post-treatment layers.

The activities the wearer regularly performs may induce a constraint on the characteristics of one or more post-treatment layers. For example, depending on whether the wearer is an office worker or an outside worker, it may be inferred whether the user is a lot outside or inside or if he changes often between inside and outside. If the wearer changes often between inside and outside, a variable tint layer may be chosen accordingly. If the wearer works a lot outside, a permanent tint layer may be chosen. Also, depending on the type of activity, the wearer may need a combination of post-treatment layers having good anti-scratch properties or other characteristics accordingly.

The parameter values acquired from the wearer may be informations relative to where the wearer lives or performs activities, i.e. geographical region or city and informations about his occupation or the activities he regularly performs.

These parameter values of the given wearer may be inferred from a questionnaire or a data base, for example.

The parameter values acquired from the given wearer are processed and a group to which the wearer belongs is inferred.

This group corresponds to a group of wearers submitted to a similar environment and to a similar activity. For example, the wearer may belong to the group of wearers living in an environment having particular environmental conditions and being a lot outside or performing activities inducing similar constraints on the choice of the combination. Other groups may refer to wearers living in different environmental conditions, being a lot inside or performing activities inducing similar constraints on the choice of the combination.

According to an embodiment, the group to which the wearer belongs may be inferred by using a decision tree, for example based on the type of activity and on the geographical region the wearer lives in.

According to another embodiment, the group to which the wearer belongs may be inferred by determining, based on the geographical region or the city of the wearer, the environmental conditions, the type of activities he performs and/or by attributing a score quantifying whether the given wearer is performing its occupation rather inside or outside, for example.

Based on the environmental conditions, the activities and/or the score determined, a group of persons having the more similar parameters may be inferred. Different groups of wearers submitted to a similar environment and to a similar activity may be determined through clustering based on the parameter values of the plurality of reference parameters. The parameter values may comprise the environmental conditions and the type of activity. The particular combination of post-treatment layers associated to each group of wearers may correspond to the combination used by a majority of reference wearers belonging to the considered group.

A particular combination of post-treatment layers may be determined based on the inferred group. The combination of post-treatment layers may be defined by a set of parameters of each layer or by a set of properties that the combination should satisfy. For example, the set of properties may concern a degree of abrasion, crazing, adherence, optical quality, anti-bacterial and anti-dust properties for example. The combination is then determined based on the set of properties corresponding to the inferred group.

Embodiment 2: Determining a Component of an Ophthalmic Equipment Based on Components Used by Reference Wearers and on the Current Equipment Used by the Wearer In this embodiment, the components previously used or currently used by reference wearers belonging to the same group of wearers as the given wearer are used to establish a list of components which could provide a good satisfaction of the given wearer when using those components.

In that case, the parameter values of the reference wearers collected in step S010 comprise features of at least one component of an ophthalmic equipment previously or currently worn by the reference wearer, and additional parameter values relating to the wearer which may be one or more of an ethnicity of the wearer, a gender of the wearer, an age of the wearer, a biometric parameter of the wearer, an activity of the wearer, an environment of the wearer, a clothing style of the wearer, a postural behavior of the wearer, prescription data of the wearer.

A satisfaction level of the reference wearer for the component considered may also be comprised within the parameter values of the reference wearers.

In step S020, the different groups of wearers are established by clustering on at least the additional parameter values of the reference wearers. According to one embodiment, in step S200, the group of wearers to which the wearer belongs is then the group, in this case the cluster, having the smallest distance to the additional parameters of the wearer, for example. According to another embodiment, the plurality of groups of wearers are defined by ranges of values of at least a subset of the parameter values and processing said acquired set of parameter values comprises determining at least one range to which a parameter value belongs and inferring the group to which the wearer belongs based on the determined range.

In steps S300 and S400, the parameter values of the reference wearers belonging to the same group of wearers as the given wearer are processed to extract a list of recommended components, defined by the features of the component previously or currently worn by the reference wearers, which gave a good satisfaction level to the reference wearers. The list may also comprise an indication of the satisfaction level obtained for the component, for example. The eyecare professional may use that list of components to recommend a specific component of the wearer.

According to another embodiment, the parameter values of the given wearer comprise features of the component currently worn by the given wearer, and optionally the associated satisfaction level, and the additional parameter values defined above. In this embodiment, the processing of the parameter values of the reference wearers belonging to the same group takes into account the component currently worn by the given wearer and optionally the associated satisfaction level, to extract a list of recommended components. These recommended components are selected because they gave a good satisfaction to the reference wearers having worn the same component as the given wearer, optionally with a similar satisfaction level as the given wearer.

The list of recommended components may be obtained using a collaborative filtering algorithm for example.

Embodiment 3: Determining a Design Parameter of the Component

As described before in reference to FIG. 1A, the at least a feature enabling to determine a component of an ophthalmic equipment of the given wearer may be a design parameter that enables to determine the component.

In that case, each set of parameter values of the reference wearers collected in step S010 further comprises, in addition to the parameter values belonging to at least two distinct categories, a design parameter that may be used for determining the component considered.

In step S020, the classification is performed on the basis of the value of the design parameter comprised within the set of parameter values of the reference wearers. The classification enables to elaborate a model for determining, based on at least a subset of parameter values belonging to at least two distinct categories, to which group of wearers the given wearer belongs and to give out accordingly the value of the corresponding design parameter. This model is used in steps S200 and steps S300 to determine to which group of wearers the given wearer belongs and to determine the value of the design parameter.

In step S400, the value of the design parameter is used to determine the component. For example, the design parameter is given as an entry parameter of a determination model which determines the features of the component.

Below are given some examples in which the classification is used to determine a design parameter.
Example: Determining a Lens Design Based on a Lowering Angle In step S010, videos of people working on laptops are collected. A set of parameters Xi and of possible parameter values (in brackets) to be determined are defined and listed below:

X1=Ethnicity=(caucasian, asian, african, indian)
X2=Gender=(female, male, other)
X3=Face shape=(oval, round, diamond, triangular)
X4=Screen size=(none, xsmall, small, medium, large, xlarge)
X5=Reading speed=(fast, normal, slow) or (below 200, from 200 to 300, above 300)
X6=Education=(defined according to International Standard Classification, obtained from social network)
X7=Typing speed=(fast, normal, slow)
X8=Age=(0-18, 18-45, 45-65, 65+)

The parameter values of the parameters Xi are determined for each reference wearer based on the collected videos and on informations gathered from a questionnaire or from social network.

An additional parameter, Y1, the gaze lowering is also determined based on the videos:
Y1=gaze lowering=(small_gaze_lowering=0-10 deg, large_gaze_lowering=10-20 deg, all_gaze_lowerings=0-20 deg)

The set of parameter values $(X_{i,\ i=1:8}, Y1)$ is determined for each of the reference wearers.

In step S020, a classification model is established based on the parameter Y1, so that, depending on the values of $X_i$, it is possible to infer in step S200 a group to which the wearer belongs, the group being defined by the value of Y1, the gaze lowering. In this example, the classification model is a decision tree determined by machine learning and implementing the decision tree enables to determine the value of the design parameter Y1. In this example, only the values of parameters X4 and X7 are relevant for the classification.

In steps S100, S200 and S300, based on the parameters values of the given wearer, which comprise the screen size and the typing speed, the gaze lowering of the wearer may be determined. It may be noted that the screen size relate to an environment of the wearer and the typing speed to a behavior of the wearer.

In step S400, based on the value of the parameter Y1, a lens designs may be determined depending on the value of Y1.

In the embodiment illustrated with this example, the design parameter value is a range and the range may be used for determining the component.

In other embodiments, the design parameter value comprised within each set of parameter values of the reference wearers may be a discrete value and the classification model may establish for each group a range of the design parameter value. In that case, it is possible to train a prediction model on the values of the design parameter as a function of the other parameter values of the set of parameter values of the reference wearers.

Embodiment 4: Determining Missing Parameters Based on the Inferred Cluster

According to an embodiment, in addition to determining at least a feature enabling to determine a component of an ophthalmic equipment of the given wearer based on the inferred group in step S300, the set of parameter values of the reference wearers belonging to the inferred group may be used to determine additional parameters of the given wearer.

These additional parameters may be determined using a prediction model as described in the preceding embodiment.

The invention claimed is:

1. A method for determining a component of an ophthalmic equipment among a set of components of an ophthalmic equipment for a given wearer, the method comprising:
acquiring a set of parameter values relating to the given wearer;
processing said acquired set of parameter values to infer a group, wherein the given wearer belongs to the inferred group and the inferred group belongs to a plurality of pre-established groups, the pre-established groups being elaborated based on respective sets of parameter values of a plurality of reference wearers having a respective satisfaction level of a component among the set of components, wherein the plurality of reference wearers comprises reference wearers having a satisfaction level higher than a predetermined threshold;

determining, using processing circuitry and based on the inferred group, at least a feature enabling to determine a component of an ophthalmic equipment of the given wearer, wherein the component belongs to the set of components of an ophthalmic equipment;

determining, using the processing circuitry, a component of an ophthalmic equipment to be used by the wearer based on at least a determined feature; and designing, using the processing circuitry, an ophthalmic equipment based on the determined component, wherein each set of parameters values of the plurality of reference wearers comprises parameter values belonging to at least two distinct categories, and wherein determining, using the processing circuitry, the component of the ophthalmic equipment to be used by the wearer based on at least the determined feature further comprises selecting the component of the ophthalmic equipment that increases a fit by the wearer.

2. The method according to claim 1, wherein the categories are relative to at least one of: an ethnicity of the wearer, a gender of the wearer, an age of the wearer, a biometric parameter of the wearer, an activity of the wearer, an environment of the wearer, a clothing style of the wearer, a postural behavior of the wearer, features of at least one component of an ophthalmic equipment previously or currently worn by the wearer, prescription data of the wearer.

3. The method according to claim 1, wherein each set of parameter values of the plurality of reference wearers further comprises the value of at least one feature enabling to determine a component of an ophthalmic equipment of each reference wearer.

4. The method according to claim 1, wherein each set of parameters values of the plurality of reference wearers further comprises at least an additional parameter value and at least an additional parameter value of the given wearer is determined based on the values of said additional parameter of the reference wearers belonging to the inferred group.

5. The method according to claim 1, wherein:
the sets of parameter values of the plurality of reference wearers comprise new sets of parameter values of new reference wearers, and
the pre-established groups are periodically actualized based on the sets of parameter values of the plurality of reference wearers comprising new sets of parameter values.

6. The method according to claim 5, wherein the acquired set of parameter values of the given wearer comprises a set of input parameter values of the given wearer and determining at least a feature comprises running a prediction model on the set of input parameter values of the given wearer.

7. The method according to claim 6, wherein the prediction model is elaborated by machine learning based on respective sets of input parameter values of the plurality of reference wearers and on the value of at least one feature of a component of an ophthalmic equipment of each of the plurality of reference wearers belonging to the inferred group.

8. The method according to claim 1, wherein the pre-established groups are elaborated by machine learning based on the respective sets of parameter values of the plurality of reference wearers.

9. The method according to claim 1, wherein processing said acquired set of parameter values comprises determining at least one range to which a parameter value belongs, and inferring the group to which the wearer belongs based on the determined range.

10. The method according to claim 1, wherein the acquired parameter values are measured and/or obtained from a questionnaire or a data base and/or extracted from online data of the wearer.

11. The method according to claim 1, wherein the components of an ophthalmic equipment are chosen from one of:
an ophthalmic lens design, wherein a lens design comprises a set of optimization parameters and/or a set of instructions configured to be used in conjunction with the prescription data to determine at least one surface of an ophthalmic lens,
a material of an ophthalmic lens,
at least a post-treatment layer, the post treatment layer being one of a variably or permanently tinted layer, an anti-breakage layer, an anti-scratch layer, an anti-reflection layer, an anti-smudge layer or an anti-fog layer,
a frame shape or material,
a control mode for an active lens,
an augmented reality equipment having a particular design.

12. A non-transitory computer readable storage medium having thereon a computer program comprising program instructions, the computer program being loadable into a processor and adapted to cause the processor to carry out, when the computer program is run by the processor, the method according to claim 1.

13. A system for determining at least a component of an ophthalmic equipment among a set of components of an ophthalmic equipment, the comprising:
processing circuitry configured to:
acquire a set of parameter values relating to the given wearer,
receive the set of parameter values relating to the given wearer,
process said acquired set of parameter values to infer a group, wherein the given wearer belongs to the inferred group and the inferred group belongs to a plurality of pre-established groups, the pre-established groups being elaborated based on respective sets of parameter values of a plurality of reference wearers having a respective satisfaction level of a component among the set of components, wherein the plurality of reference wearers comprises reference wearers having a satisfaction level higher than a predetermined threshold,
determine, based on the inferred group, at least a feature enabling determination of a component of an ophthalmic equipment of the given wearer, wherein the component belongs to the set of components of an ophthalmic equipment,
determine a component of an ophthalmic equipment to be used by the wearer based on at least a determined feature, and
design an ophthalmic equipment based on the determined component,
wherein each set of parameters values of the plurality of reference wearers comprises parameter values belonging to at least two distinct categories,
wherein the processing circuitry is further configured to determine the component of the ophthalmic equipment to be used by the wearer based on at least the determined feature by being configured to select the component of the ophthalmic equipment that increases a fit by the wearer.

\* \* \* \* \*